US010151702B2

(12) United States Patent
Jones

(10) Patent No.: US 10,151,702 B2
(45) Date of Patent: Dec. 11, 2018

(54) NANOFIBER SPECTRAL ANALYSIS

(71) Applicant: Halliburton Energy Services, Inc., Houston, TX (US)

(72) Inventor: Christopher Michael Jones, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 213 days.

(21) Appl. No.: 14/588,757

(22) Filed: Jan. 2, 2015

(65) Prior Publication Data

US 2015/0115146 A1 Apr. 30, 2015

Related U.S. Application Data

(63) Continuation of application No. 13/390,651, filed as application No. PCT/US2009/054605 on Aug. 21, 2009, now abandoned.

(51) Int. Cl.
*G01V 8/00* (2006.01)
*G01N 21/64* (2006.01)
(Continued)

(52) U.S. Cl.
CPC ............ *G01N 21/648* (2013.01); *B82Y 15/00* (2013.01); *B82Y 20/00* (2013.01); *E21B 47/123* (2013.01);
(Continued)

(58) Field of Classification Search
CPC ...... G01N 21/648; G01V 8/24; E21B 47/123; B82Y 15/00
See application file for complete search history.

(56) References Cited

U.S. PATENT DOCUMENTS 4,604,222 A * 8/1986 Borduz ................ H01F 1/44
252/62.51 R
4,894,532 A * 1/1990 Peterson ............ G01N 21/7703
250/226
(Continued)

FOREIGN PATENT DOCUMENTS

AU 2009351544 B2 1/2014
EP 1804052 A1 7/2007
(Continued)

OTHER PUBLICATIONS

"European Application Serial No. 15158534.6, Extended European Search Report dated Jul. 15, 2015", 7 pgs.
(Continued)

*Primary Examiner* — David P Porta
*Assistant Examiner* — Shun Lee
(74) *Attorney, Agent, or Firm* — Gilliam IP PLLC

(57) ABSTRACT

Apparatus, systems, and methods may operate to transmit energy to a nanofiber sampling coil and/or a nanofiber reference coil. Further activity may include receiving the energy as modified by evanescent interaction with a sampled material located proximate to the sampling coil and/or as modified by propagation through the reference coil, and comparing the energy modified by evanescent interaction with the energy modified by propagation through the reference coil to determine a spectroscopic property of the sampled material. Additional apparatus, systems, and methods, including the use of nanofibers and fluorescence induced by evanescent radiation to conduct spectroscopic analysis, are disclosed.

19 Claims, 7 Drawing Sheets

(51) Int. Cl.
| | |
|---|---|
| *B82Y 15/00* | (2011.01) |
| *B82Y 20/00* | (2011.01) |
| *E21B 47/12* | (2012.01) |
| *G01V 8/24* | (2006.01) |
| *G01N 21/80* | (2006.01) |

(52) U.S. Cl.
CPC .............. *G01V 8/24* (2013.01); *G01N 21/80* (2013.01); *G01N 2021/6417* (2013.01); *G01N 2021/6419* (2013.01); *G01N 2021/6484* (2013.01); *G01N 2201/08* (2013.01); *G01N 2201/088* (2013.01); *Y10S 977/954* (2013.01)

(56) References Cited

U.S. PATENT DOCUMENTS

| | | | | |
|---|---|---|---|---|
| 4,957,371 | A * | 9/1990 | Pellicori | G01J 3/12 |
| | | | | 250/226 |
| 5,097,129 | A * | 3/1992 | de Vries | G01N 21/552 |
| | | | | 250/227.14 |
| 5,168,156 | A | 12/1992 | Fischer et al. | |
| 5,225,887 | A * | 7/1993 | Lipson | G01D 5/266 |
| | | | | 250/227.19 |
| 5,306,909 | A | 4/1994 | Jones et al. | |
| 6,075,611 | A | 6/2000 | Dussan, V et al. | |
| 6,388,251 | B1 * | 5/2002 | Papanyan | E21B 47/102 |
| | | | | 250/256 |
| 6,437,326 | B1 | 8/2002 | Yamate et al. | |
| 6,467,340 | B1 | 10/2002 | Gallagher et al. | |
| 6,627,873 | B2 | 9/2003 | Tchakarov | |
| 6,683,681 | B2 | 1/2004 | DiFoggio et al. | |
| 6,995,360 | B2 | 2/2006 | Jones | |
| 7,016,026 | B2 | 3/2006 | DiFoggio et al. | |
| 7,142,306 | B2 | 11/2006 | Wu | |
| 7,266,259 | B1 | 9/2007 | Sumetsky | |
| 7,336,859 | B2 | 2/2008 | Sanders | |
| 2002/0043620 | A1 | 4/2002 | Tchakarov et al. | |
| 2002/0176646 | A1 * | 11/2002 | Wu | G01F 1/7086 |
| | | | | 385/12 |
| 2003/0193662 | A1 | 10/2003 | DiFoggio et al. | |
| 2005/0269499 | A1 | 12/2005 | Jones et al. | |
| 2006/0132792 | A1 | 6/2006 | Schultz et al. | |
| 2007/0147732 | A1 | 6/2007 | Sanders | |
| 2007/0148760 | A1 | 6/2007 | Klesel et al. | |
| 2008/0087078 | A1 | 4/2008 | Vannuffelen et al. | |
| 2009/0049904 | A1 | 2/2009 | Meister | |
| 2009/0059233 | A1 | 3/2009 | Sumetsky | |
| 2009/0068668 | A1 | 3/2009 | Duer | |
| 2011/0043818 | A1 * | 2/2011 | Sumetsky | G01D 5/35329 |
| | | | | 356/477 |
| 2012/0223221 | A1 | 9/2012 | Jones | |

FOREIGN PATENT DOCUMENTS

| | | |
|---|---|---|
| WO | WO-2006054117 A2 | 5/2006 |
| WO | WO-2011022020 A1 | 2/2011 |

OTHER PUBLICATIONS

"Malaysian Application Serial No. PI2012000558, Office Action dated May 15, 2014", 4 pgs.
Nayak, K P, et al., "Optical nanofiber as an efficient tool for manipulating and probing atomic fluorescence References and links", *Optics Express*, vol. 15, No. 9, (Apr. 19, 2007), 5431-5438.
"U.S. Appl. No. 13/390,651, Advisory Action dated Apr. 5, 2013", 3 pgs.
"U.S. Appl. No. 13/390,651, Advisory Action dated Sep. 11, 2014", 3 pgs.
"U.S. Appl. No. 13/390,651, Applicant's Summary of Examiner Interview filed Jun. 27, 2014", 2 pgs.
"U.S. Appl. No. 13/390,651, Applicant's Summary of Examiner Interview filed Sep. 26, 2014", 1 pg.
"U.S. Appl. No. 13/390,651, Final Office Action dated Jan. 28, 2013", 17 pgs.
"U.S. Appl. No. 13/390,651, Final Office Action dated Jul. 11, 2014", 23 pgs.
"U.S. Appl. No. 13/390,651, Non Final Office Action dated Oct. 18, 2012", 17 pgs.
"U.S. Appl. No. 13/390,651, Non Final Office Action dated Dec. 26, 2013", 22 pgs.
"U.S. Appl. No. 13/390,651, Preliminary Amendment filed Feb. 15, 2012", 7 pgs.
"U.S. Appl. No. 13/390,651, Respnse filed Aug. 18, 2014 to Final Office Action dated Jul. 11, 2014", 18 pgs.
"U.S. Appl. No. 13/390,651, Response filed Mar. 28, 2013 to Final Office Action dated Jan. 28, 2013", 10 pgs.
"U.S. Appl. No. 13/390,651, Response filed May 27, 2014 to Non Final Office Action dated Dec. 26, 2013", 19 pgs.
"U.S. Appl. No. 13/390,651, Response filed Jun. 27, 2013 to Advisory Action dated Apr. 5, 2013", 17 pgs.
"U.S. Appl. No. 13/390,651, Response filed Oct. 9, 2014 to Advisory Action dated Sep. 11, 2014", 15 pgs.
"U.S. Appl. No. 13/390,651, Response filed Dec. 10, 2012 to Non Final Office Action dated Oct. 10, 2012", 12 pgs.
"Australian Application No. 2009351544, First Examiner's Report dated Nov. 2, 2012", 6 pgs.
"European Application Serial No. 09848571.7, Examination Notification Art. 94(3) dated Jan. 29, 2014", 6 pgs.
"European Application Serial No. 09848571.7, Office Action dated Aug. 5, 2013", 6 pgs.
"European Application Serial No. 09848571.7, Office Action dated Jan. 2, 2013", 1 pg.
"European Application Serial No. 09848571.7, Reply filed Jun. 27, 2013 to Office Action dated Jan. 2, 2013 and European Search Report dated Dec. 14, 2012", 20 pgs.
"European Application Serial No. 09848571.7, Reply filed Jul. 28, 2014 to Examination Notification Art. 94(3) dated Jan. 29, 2014", 24 pgs.
"European Application Serial No. 09848571.7, Response filed Dec. 16, 2013 to Office Action dated Aug. 5, 2013", 17 pgs.
"European Application Serial No. 09848571.7, Supplementary European Search Report dated Dec. 14, 2012", 10 pgs.
"International Application Serial No. PCT/US2009/054605, International Preliminary Report on Patentability dated Mar. 1, 2012", 6 pgs.
"International Application Serial No. PCT/US2009/054605, Search Report dated Oct. 20, 2009".
"International Application Serial No. PCT/US2009/054605, Written Opinion dated Oct. 20, 2009".
"Malasian Application U.S. Appl. No. PI2012000558, Response filed Jun. 27, 2014 to Office Action dated May 15, 2014", (w/ English Translation of Amended Claims), 10 pgs.
"Nanofiber", [online]. Wikipedia. [retrieved on Oct. 28, 2012]. Retrieved from the Internet:: <URL://http://en.wikipedia/org/wiki/Nanofiber>, (2012), 4 pgs.
"Subwavelength-diameter optical fibre", [online]. Wikipedia. [retrieved on Dec. 4, 2012]. Retrieved from the.Internet: <URL: http://en.wikipedia.org/w/index.php?title=Special:Book&bookcmd=download&collection_id=4c78485adc0f86168&writer=rl&return_to*Subwavelength-diameter optical fibre>, (Dec. 4, 2012), 6 pgs.
Brambili, G., "Optical fibers go nano", Laser Focus World, (Oct. 2007), 85-88.
Ghandehari, M., et al., "In situ monitoring of pH level with fiber optic evanescent field spectroscopy", NDT & E International, 37(8), (Dec. 2004), 611-616.
Sumetsky, M, "Optical Micro- and Nanofibers for Sensing Application", Proceedings of SPIE vol. 6556, (Apr. 2007), 65560J-1-65560J-11.
Sumetsky, M., "Basic Elements for Microfiber Photonics: Micro/Nanofibers and Microfiber Coil Resonators", Journal of Lightwave Technology, 26(1), (2008), 21-27.

* cited by examiner

NANOFIBER SPECTRAL ANALYSIS

PRIORITY APPLICATIONS

This application is a continuation of U.S. patent application Ser. No. 13/390,651, filed 15 Feb. 2012, which application is a U.S. National Stage Filing under 35 U.S.C. 371 from International Application No. PCT/US2009/054605, filed on Aug. 21, 2009, and published as WO 2011/022020 A1 on Feb. 24, 2011; which applications and publication are incorporated herein by reference in their entirety

BACKGROUND

Spectroscopic analysis in a downhole environment sometimes makes use of a window or window surface total internal reflection to examine various sample materials. Both configurations may use instrumentation of substantial size, since the light sources used tend to be of low intensity, leading to the use of optics that concentrate light source output for greater resolution.

Windows have disadvantages when used in high-pressure environments, such as the difficulty of configuring the window mounting aperture to be pressure-tight, and keeping the window surface clean in the face of particle accumulation. Scattering via particles can greatly reduce the transmitted signal.

To reduce the overall size of the apparatus involved, windowed configurations may be designed to trade a reduced path length for reduced sensitivity. When total internal reflection is used, path lengths may be even more limited. For example, the sampling depth in a given material may be limited to approximately one-third of the wavelength of the light used in the analysis.

While these difficulties with performing spectroscopic analysis may be compounded when attempted in a downhole environment, it should be noted that many of these problems are not unique to the petroleum recovery industry. That is, they are common to many spectroscopic and photometric analysis designs, including those used for industrial in-line monitoring systems.

DETAILED DESCRIPTION

Figure 1:
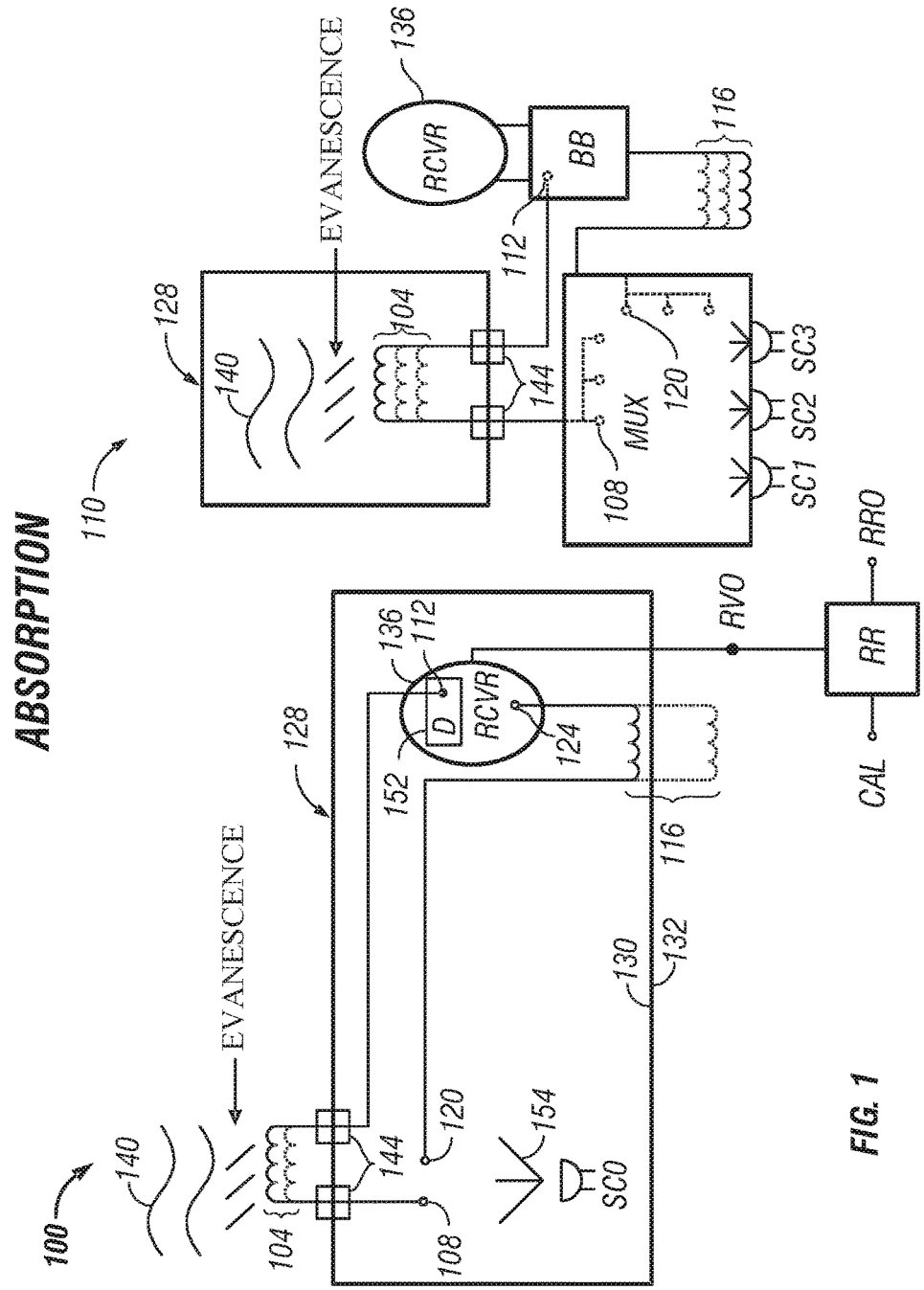
FIG. 1 illustrates a block diagram of absorption apparatus according to various embodiments of the invention.

In most embodiments, nanofibers can be used as part of a spectrographic analysis apparatus to overcome some of the difficulties noted above. This can be useful in downhole environments, where high temperature and pressure can be present. Many other analysis environments can also benefit.

Evanescent electromagnetic fields are an extension of electromagnetic radiation outside of the medium which carries the electromagnetic radiation. For example, evanescent field production can occur via total internal reflection. This form of evanescent field spectroscopy has been commercialized in the form of attenuated total internal reflection spectroscopy.

Evanescent fields can also be produced when the reflection of electromagnetic energy occurs at the boundary of materials with different indices of refraction, such as when the index of refraction of the medium that carries the energy is greater than the index of refraction of a material behind the reflective surface. Generally, the extent of the evanescent field is about one-third of a wavelength of the radiation being reflected. Therefore the "sampling depth" of the total internal reflection is usually on the order of nanometers for near infrared radiation, to a few micrometers for mid to far infrared radiation.

In many of the embodiments described herein, the evanescent electromagnetic radiation field is produced using optical media, such as fiber optics, where the shortest dimension of the medium (e.g., the diameter of the fiber for optical fibers) is less than the wavelength of the radiation.

Until recently the diameter of optical fibers was much greater than most common spectroscopic radiation analysis wavelengths. That is, until recently no optical fiber existed with diameters less than the wavelengths exhibited by mid to near infrared sources. However, methods are now available to produce optical fibers with diameters of 60 to 100 nm (about 4 times smaller than visible light wavelengths, and about 10 times smaller than near infrared light wavelengths).

Nanofibers have many interesting characteristics. For example, nanofibers are at once strong and flexible. They can have very small bend radii (e.g., in the micrometer range), permitting the construction of very compact devices. Diffraction (instead of reflection) is responsible for providing the evanescent field, and up to 99% of the available optical power can be transmitted outside the medium boundary when evanescent radiation is present. Thus, there can be a relatively high intensity of light in the evanescent field arising from common light sources, sometimes approaching laser intensities.

Spatial decay of the evanescent field in nanofibers is greatly extended, so that fiber diameter controls sampling depth, and not wavelength. For example, evanescent fields may extend more than 100 times the radius of the fiber at 1.55 micrometers (i.e., near infra-red). The sampling depth in this case is therefore about 10 micrometers for a nanofiber, as opposed to 0.5 micrometers for total internal reflection—an improvement of twenty times.

When a material sample is placed proximate to a nanofiber that has been position to received illuminating energy, the energy follows the fiber, and evanescent radiation interacts with the sample. Thus, when small bend radii are used in a coiled nanofiber, the illuminating energy loops around the inner surface of the fiber and extends the total path length of evanescent interaction with a sample by many times, perhaps several thousand. Therefore, a few millimeters of coiled nanofiber can operated to extend the absorption length of energy transmitted through the fiber to meters.

Nanofibers often facilitate connection to other optical components because the ends of the nanofiber can be made in a conventional size. This leads to detection limits on the order of one part in $10^7$ absorbance units. The chemical species under examination can be taken into account to convert the absorbance units to concentration units.

The windows of conventional spectroscopic analyzers can become coated with particles due to the existence of Van der Waals forces, which are related to the area of interaction and the translational energy of the particles. Thus, smaller particles tend not to stick to nanofibers because of the greater available translational motion of the particles. In addition, because of their (relatively) small radius of curvature, larger particles also tend not to stick. These characteristics allow nanofibers to be more resistant to the buildup of material on their surface.

Surfaces in general may be cleaned of particle buildup by a variety of methods. One method is through translational excitation of the buildup particles. That is, when a wavelength of light approaches the size of a particle, the particle as a whole may be excited along transitional modes. If the light is of sufficient intensity, then the light may excite the particles coating a surface with enough translational motion to overcome the forces of interaction. However, an intense pulse of light may be needed to clean the surface, and the wavelength of light should be of the proper size for a given particle size. For conventional surfaces, the distribution of particle size on a surface may be large, such that the corresponding distribution of wavelengths used to clean the surface is also large. This can result in diluting the intensity of a cleaning light pulse because the power of the pulse is distributed among more frequencies.

The distribution of particle sizes that can adhere to a nanofiber surface is greatly reduced (in comparison to a window), so that pulses of cleaning light can be narrowed in their frequency distribution, perhaps increasing the intensity of the light for a given power, with a commensurate increase in cleaning efficiency.

Optical sampling with nanofibers is suited to both absorption, emission (florescence, etc.), and scattering spectroscopy. The small scale dimensions of optical nanofibers allow the construction of multiple optical paths within a compact confined volume. New configurations of multivariate optical spectrometers, not previously practical with conventional techniques, can now be constructed. For example, in some embodiments that use a broadband light source, wavelength discrimination of the detected light is not needed, because multiple nanofibers can be used to sample the "same" fluid over the nanoscale regions occupied by the nanofibers. Some embodiments take advantage of the long distance evanescent field to excite and detect florescence using nanofiber pairs or nanofiber-standard fiber pairs.

In some embodiments, apparatus using nanofibers are used to facilitate compositional analysis of a fluid down hole. The fluid may comprise a liquid, or gas, or both. The presence of particles in the fluid may also be detected. such detectors may be used to discriminate separate phases of the fluid volumetrically. The resultant spectrum may provide composition of an organic phase including, but not limited to, C1, C2-C15 pseudo distribution, and C16+.

Since many macroscopic properties of oils depend on composition, the results of spectral analysis using nanofibers can be directly correlated to properties such as the gas-oil ratio (GOR), bubble point, viscosity, American Petroleum Institute (API) gravity, wax appearance point, asphaltene appearance point, etc. Generally, the spectrum of an oil is matrix dependent. However, many macroscopic properties of oils are also matrix dependent. Therefore, a direct correlation of macroscopic properties to spectral characteristics often yields a better result than attempting to correlate components and pseudo-components to macroscopic oil properties.

The spectroscopy of the water in a water phase may yield water composition properties as well as macroscopic properties, including but not limited to the ion chemistry (cations and anions), such as dissolved organics and organic acids, total dissolved solids, dissolved gases, etc. The spectroscopy of the organic or water phase may also yield information regarding drilling fluid contamination. Through multivariate curve resolution, or a related technique such as trilinear decomposition, or time evolved factor analysis as well as principal component markers or eigenvector markers, the end members of the pure drilling fluid (or pure formation water or pure crude oil) need not be known a priori when analysis using nanofibers occurs.

FIG. 1 illustrates a block diagram of absorption apparatus 100, 110 according to various embodiments of the invention. Here it can be seen that the apparatus 100, which operates primarily via diffraction-induced evanescence, comprises one or more sampling nanofibers 104, perhaps formed into a sampling coil having a first sampling end 108 and a second sampling end 112. The apparatus 100 includes one or more reference nanofibers 116, perhaps formed into a reference coil having a first reference end 120 and a second reference end 124.

The apparatus 100 may further comprise a chamber 128 defined by an inner surface 130 that is completely enclosed by an outer surface 132. The chamber 128 may comprise a pressure-tight chamber that is designed to prevent the incursion or escape of liquid or gas under pressure. "Pressure-tight" as used herein means that the chamber 128 is designed to maintain a pressure differential between the pressure on the inner surface 130 and the pressure on the outer surface 132 without substantial leakage between the inside of the chamber 128, and the outside of the chamber 128.

In apparatus 100, the first and the second sampling ends 108, 112 are disposed within the chamber 128, and the sampling coil is disposed outside the chamber 128. The reference nanofiber 116 may be disposed inside or outside the chamber 128.

The apparatus 100 may further comprise one or more energy sources SC0 to direct energy to at least one of the first sampling end 108 or the first reference end 120. The apparatus 100 may also comprise a receiver 136 to receive at least one of the energy modified by evanescent interaction with a sampled material 140 (e.g., a fluid) located within an inner diameter of the sampling coil or outside an outer diameter of the sampling coil, or the energy modified by propagation through the reference coil.

Thus, in an elementary form, some apparatus 100 comprise two nanofibers: one used to provide evanescent energy to the sample, and one used as a reference. One or both of the nanofibers may be coiled, or not. An energy source SC0 is used to excite both fibers, and a receiver 136 is used to receive the energy from both fibers. Evanescent interaction occurs both inside and outside the sampling coil, when such a coil is constructed. The sampled material 140 can form part of a fluid flow comprising a fluid of liquid, gas, or both.

A "nanofiber" is defined herein as an optical fiber having a diameter of less than half of the wavelength of the energy it carries. This means that many nanofibers will have a diameter that is less than 100 nm, and in some cases, less than 50 nm. A reduced fiber diameter with respect to the wavelength of energy the fiber caries can increase diffraction, and thus, diffraction-based evanescence.

A reference nanofiber 116 is not used in all embodiments, however, its presence can be useful. The reference nanofiber 116 may be located within a fluid sampling path or external to the fluid sampling path. If located within the fluid sampling path, the reference nanofiber 116 may have cladding to prevent interaction with energy in the fluid, while still experiencing the temperature and pressure effects of the fluid being sampled. In some embodiments, the reference nanofiber 116 may have a different coil diameter and or different core diameter or a different total length than the sampling nanofiber 104.

In some embodiments, as shown for the apparatus 110, such as when in-line sampling for chemical processes is used, or in a laboratory, the sampling nanofiber 104 can be located inside the chamber 128, and the sampling ends 108, 112 can be located external to the chamber 128. In this case, the sampled material 140 is contained within the chamber 128, instead of being external to it.

Many variations are possible. For example, light energy from multiple broadband sources SC1, SC2, SC3 with orthogonal wave functions (i.e., where the intensity verus wavelength characteristics of the independent sources are not linear combinations of each other) can be used to impinge on separate proximal ends of multiple sampling nanofibers 104. Energy from multiple broadband sources SC1, SC2, SC3 can also interact with multiple reference nanofibers 116 simultaneously.

Some or all of the nanofibers may extend through a pressure-tight barrier 144 into a fluid. The barrier 144 may comprise a ferromagnetic seal to seal the sampling nanofiber 104 and/or the reference nanofiber 116 against the inner surface 130 of the chamber 128, for example.

A ferromagnetic seal can be useful because it reduces the differential stress on the fiber itself. One of the difficulties encountered in pressure feed-through systems for optical fibers (e.g., low pressure to high pressure) occurs when an epoxy is used to seal the fiber against the wall of the chamber. Although the surface area of the fiber fed through the wall is sufficiently small that force on the fiber and epoxy is small, and high pressure sealing (beyond 400 MPa) is achievable, when the system heats or cools, the thermal expansion differential between the wall and fiber can break the fiber.

A ferromagnetic fluid can be used seal large pressure differentials across relatively small sectional areas. This can be useful for nanofibers, where the cross-sectional sealing area is small, and the fiber is free to slip against the wall to mitigate differential stresses. In some embodiments, the nanofiber is coated in a magnetic or magnetism-inducing material.

When coils are formed in nanofibers, the diameter of the coils may be arranged according to the wavelengths of energy provided by the sources SC0 ... SC3. Multiple-helix coils can be arranged so that individual loops in the coil are spaced apart at a distance that is greater than the evanescent field length.

The source of energy SC0 ... SC3 is not monochromatic in some embodiments. When the energy 154 is returned to impinge on the receiver 136, no separation of the energy 154 into wavelengths prior to sample interaction or after sample interaction is used in some embodiments. However, in some cases, the receiver 136 may be designed for greater sensitivity with respect to specific wavelengths of energy carried in the fibers 104, 116.

The receiver output RVO of the receiver 136 for each sampling-reference fiber pair can be separated using an analog circuit or digitized for analysis. In some embodiments, the receiver 136 may comprise a plurality of detectors (not shown) with specific wavelength response factors to create a multivariate signal as the output RVO.

The output from pairs of fibers can be balanced using a balancing bridge BB (e.g., a Wheatstone bridge or similar configuration) coupled to the sampling nanofiber(s) 104 and the reference nanofiber(s) 116. Response output(s) RVO from the receiver 136 may be regressed to an appropriate multivariate calibration using a response regression module RR having analog or digital circuitry. The response regression module RR can be used to receive the output RVO from the receiver 136 and to provide a regression output RRO based on a calibration input CAL and the receiver output RVO.

In many embodiments, an electrical bridge BB will be used on the receiver 136 to balance the received sample energy versus the received reference energy. Optical balancing is also possible via optical circuit equivalents.

Prior to reception, received energy 154 that was originally provided by a broadband source may be discriminated using a discriminator 152. Thus, a wavelength discriminator 152 may be interposed between the second sampling end 112 and the receiver 136. In some embodiments, the sources SC0 ... SC3 may comprise a monochromatic light source, perhaps one with a variable wavelength output. Multiple energy sources SC1 ... SC3 may be multiplexed using a multiplexer MUX. Thus, a plurality of energy sources SC1 ... SC3 may be coupled to a multiple-input, single-output multiplexer MUX.

In some embodiments, the sampling nanofiber 104 may be coated with a material that is selectively interactive with components of the material 140 that is being sampled, or that changes its properties based on macroscopic properties of the material 140. For example, the sampling nanofiber 104 may be bound to or covered with or be placed in close proximity to a pH-selective compound, or an ion-selective compound. Such compounds may include zeolites and/or other ion-exchange media well known to those of ordinary skill in the art. The compounds may be designed to change interaction properties based on temperature or pressure. The pH-selective compound, or an ion-selective compound may be attached to the fiber as a relatively thin (partial or full) coating in some embodiments, or as a thicker coating that becomes a separate structure which completely covers the nanofiber 104. Still more embodiments may be realized.

For example, the energy source SC0 ... SC3 may comprise a plurality of broadband sources having orthogonal wave functions, wherein the energy 154 comprises a corresponding plurality of energies directed to a corresponding plurality of sampling nanofibers 104. Similarly, a plurality of energies 154 may be directed to a corresponding plurality of reference nanofibers 116.

In some embodiments, the energy source SC0 ... SC3 may comprises a broadband energy source or a substantially monochromatic source, including a frequency tunable, substantially monochromatic source. The energy source SC0 ... SC3 may also comprise a plurality of substantially monochromatic sources to provide the energy 154 as a corresponding plurality of energies directed to a corresponding plurality of sampling nanofibers 104.

The receiver 136 may comprise a tunable receiver to resolve a plurality of wavelengths in the energy 154 provided by the broadband energy source, or a plurality of receivers/detectors corresponding to a plurality of reception wavelength sensitivities.

In one embodiment, the apparatus 100 may comprise a plurality of sampling nanofibers 104 formed into a corresponding plurality of sampling coils, at least two of the plurality of sampling coils having different coil diameters corresponding to different sensitivity wavelengths, and a spacing between loops in the at least two of the plurality of coils greater than one evanescent wavelength associated with one of the at least two of the plurality of coils. The sampling nanofibers 104 may be partially or fully-coated with, or be placed in close proximity to a pH-selective compound or an ion-selective compound.

Figure 2:
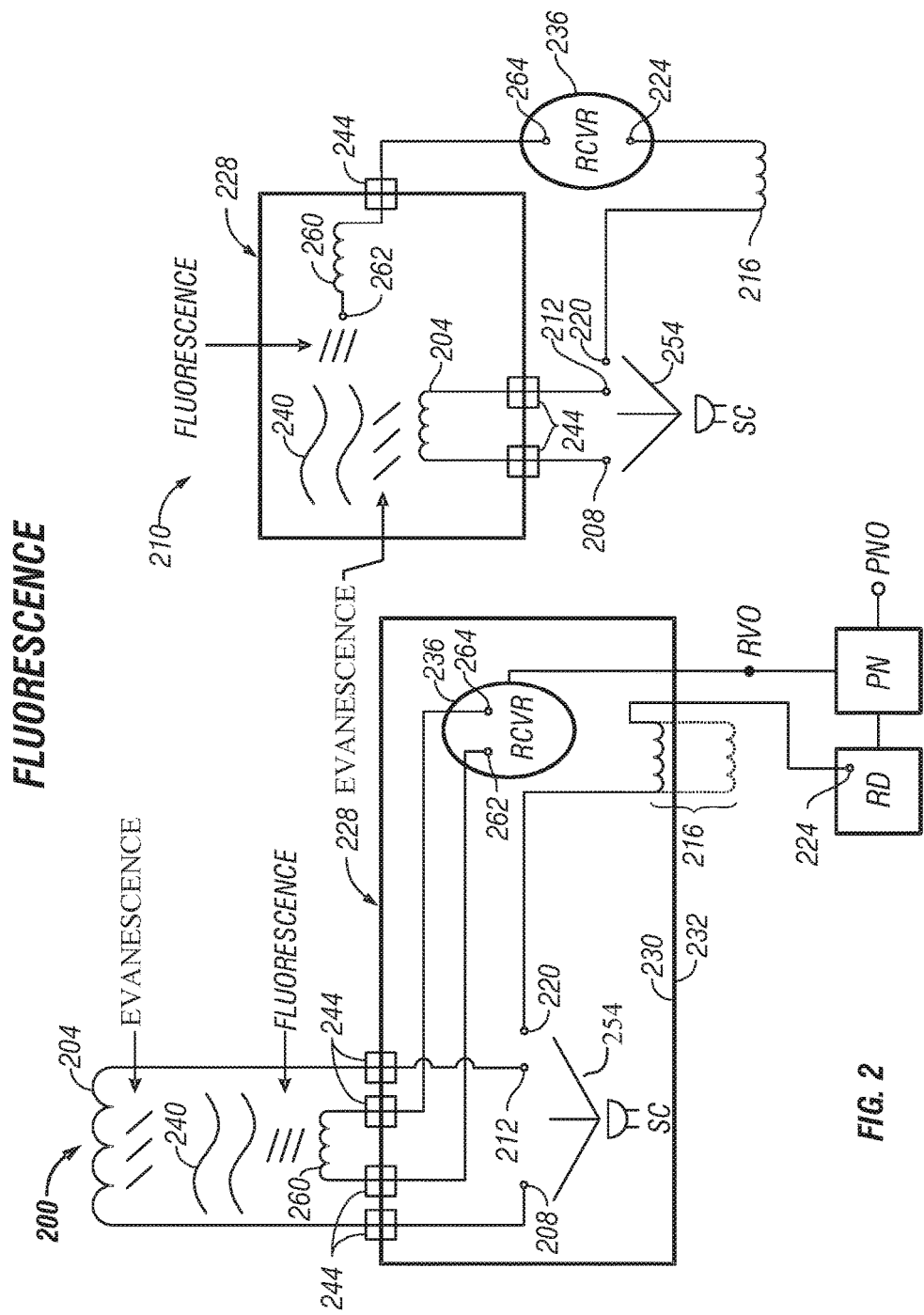
FIG. 2 illustrates a block diagram of fluorescence apparatus according to various embodiments of the invention.

FIG. 2 illustrates a block diagram of fluorescence apparatus 200, 210 according to various embodiments of the invention. Here it can be seen that the apparatus 200, which operates primarily via evanescence-induced fluorescence, comprises one or more fluorescence nanofibers 204 having a first fluorescence end 208 and a second fluorescence end 212. The apparatus 200 may further comprise one or more probe fibers 260, a portion of which may be disposed within 100 fluorescence nanofiber diameters of the fluorescence nanofiber 204. In some embodiments, the distance between the fibers 204, 260 may be reduced to some distance less than this. The probe fiber 260 has a first probe end 262 and a second probe end 264. The probe fiber 260 may comprise a wavelength-discriminating probe fiber in some instances.

The apparatus 200 may further comprise a chamber 228 (e.g., a pressure-tight chamber) defined by an inner surface 230 that is completely enclosed by an outer surface 232. In the apparatus 200, the first and the second fluorescence ends 208, 212 are disposed within the chamber 228, and a portion of the fluorescence nanofiber 204 and a portion of the probe fiber 260 are each disposed outside the chamber 228.

The apparatus 200 may further comprise one or more energy sources SC to direct source energy having a selected fluorescence frequency to the first fluorescence end 208, and/or second fluorescence end 212. The apparatus 200 may comprise a receiver 236 to receive fluorescence energy via the probe fiber 260, the fluorescence energy provided by a sampled material 240 disposed proximate to the fluorescence nanofiber 204 and the probe fiber 260.

The sampled material 240 can be used to provide fluorescence energy in response to evanescant energy arising from the source energy present in the fluorescence nanofiber 204. It should be noted that while the fiber comprising the fluorescence nanofiber 204 has been described as a nanofiber, the fiber comprising the probe fiber 260 has not. This is because in most embodiments, the probe comprises a regular optical fiber. However, in some embodiments, the probe fiber 260 comprises a nanofiber.

One or both of the probe ends 262, 264 may be disposed to provide some of the received fluorescence energy to the receiver 236. For example, some portion of the probe fiber 260 may be covered with cladding, or not. If it is covered more or less completely, then one end 262 of the probe fiber 260 can be used to deliver the fluorescence energy to the receiver 236. If the probe fiber 260 is unclad along some portion, then both ends 262, 264 of the probe fiber can be used to deliver the fluorescence energy to the receiver 236, since the fluorescence energy can be received along the unclad portion.

Thus, in an elementary form, the apparatus 200 comprises a fluorescence nanofiber 204 to induce fluorescence in a sampled material 240 via evanescent energy, and a probe fiber 260 to receive the fluorescence energy that results. No reference fiber 216 is used in many embodiments. The probe fiber 260 can be any diameter. The ends 208, 212 of the fluorescence nanofiber 204 allow fluorescent wavelengths from the source SC to be coupled to the central body of the fluorescence nanofiber 204.

The probe fiber 260 may have an index of refraction that is greater than the fluorescence nanofiber 204 index of refraction. However, depending on the index of refraction of the material 240 being sampled, there are also embodiments where the probe fiber 260 has an index of refraction that is less than that of the fluorescence nanofiber 204. The probe fiber 260 may be coated with a material that is selectively interactive with components of the material 240 that is being sampled, or that changes its properties based on macroscopic properties of the material 240.

In some embodiments 210, such as those used for in-line monitoring and laboratory use, the fluorescence nanofiber 204 may be located inside of the chamber 228, with the fluorescence ends 208, 212 located outside the chamber 228. In this case, the sampled material 240 is disposed within the chamber 228, rather than outside of it.

To conduct a spectroscopic analysis, energy 254 of sufficient wavelength to achieve florescence of a desired component or components in the sampled material 240 is made to impinge an optical nanofiber (e.g., the florescence nanofiber 204. Light from the energy source SC can also interact with a reference fiber 216 simultaneously, if desired.

The florescence nanofiber 204 and the probe fiber 260 can pass through a pressure housing, such as the chamber 228, into a fluid or other material 240 to be sampled. In some embodiments, the fluorescence nanofiber 204 can be wrapped around a larger probe fiber 260. In some embodiments, a plurality of fluorescence nanofibers 204 may each be wrapped at least partially around the probe fiber 260. In this case, the receipt of energy by the florescence nanofibers may be time-gated. The probe fiber 216 may also be formed as a coil, inside of which the fluorescence nanofiber 204 is disposed.

The florescence nanofiber interacts with material 240 to induce fluorescent emission (e.g., via evanescent radiation) from optically excited components in the material 240. The fluorescent emissions are received into the probe fiber 260, either via an end 262 of the probe fiber 260, or perhaps through an unclad portion of the probe fiber 260.

One or both ends 262, 264 of the probe fiber 260 may return through a wall of the chamber 228 to direct the received fluorescence energy to impinge on the receiver 236. The concentration of components excitable by florescence in the sampled material 240 can be directly related to the amount of florescence energy induced, and the intensity of the energy (e.g., evanescent) inducing florescence. Thus, in some embodiments, the fluorescence energy received at the receiver is normalized by the power output of a reference fiber 216.

In some embodiments, multiple fiber pairs may be used in a similar manor to the absorption embodiment (e.g., apparatus 100, 110 in FIG. 1), with multiple florescence broadband sources SC. Multiple sources and receiver components have not been shown in FIG. 2 to prevent obscuring details of various embodiments. For this same reason, multiple receivers 136, 236, and multiple detectors in a single receiver, have not been shown in either of FIGS. 1, 2.

The energy source SC may comprise a tunable energy source to provide the source energy 254 comprising any one of a plurality of fluorescence frequencies. If multiple sources SC are used, they may be multiplexed (not shown in FIG. 2, but see FIG. 1). Thus, the apparatus 200, 210 may comprise a multiplexed energy source SC to direct the source energy 254 comprising any one of a plurality of fluorescence frequencies to one or more fluorescence nanofibers 204.

Selected, specific bands of florescence may be used in multiple florescence fibers 204. Similarly, selected, specific probe bands may be observed by one or more receivers 236 if the probe fiber 260 is wavelength discriminated.

Two florescence nanofibers 204 (not shown) may be located within the evanescent field interaction distance for double-florescence excitation. Attenuation of light in the second florescence fiber may be indicative of the second florescence step. A flux may be determined by placing multiple probe fibers 216 (not shown) spatially along a single axis with respect to the flow of sampled material.

In some embodiments, the receiver 136 may comprise a plurality of detectors (not shown) with specific wavelength response factors to create a multivariate signal as the output signal RVO.

Some or all of the nanofibers may extend through a pressure-tight barrier 244 into a fluid or other sampled material 240. The barrier 244 may comprise a ferromagnetic seal to seal the fluorescence nanofiber 204, the probe fiber 260, and/or the reference fiber 216 against the inner surface 230 of the chamber 228.

In some embodiments, the fluorescence nanofiber 204 may be coated with a material that is selectively interactive with components of the material 240 that is being sampled, or that changes its properties based on macroscopic properties of the material 240. For example, the fluorescence nanofiber 204 may be bound to or covered with a pH-selective compound, or ion-selective compound. The compound may be designed to change its interaction properties based on temperature or pressure. Still more embodiments may be realized.

For example, the fluorescence nanofiber 204 may be formed into a fluorescence coil between the first and second fluorescence ends 208, 212. A portion of the probe fiber 260 may comprise an unclad portion disposed within a fluorescence nanofiber 204 coil. The probe fiber 260 may also be formed into a probe coil, and some portion of the fluorescence nanofiber 204, also formed as a coil, may be disposed within the probe coil.

In some embodiments, the apparatus 200 comprises one or more reference fibers 216 having a first reference end 220 to receive the source energy 254, and a second reference end 224 to direct the source energy 254 to a reference detector RD. The apparatus 200 may also comprise a power normalizer PN to normalize the output RVO of the receiver based on the output of the reference detector RD, providing a normalized output PNO.

In some embodiments, the energy source SC can provide source energy 254 at multiple fluorescence frequencies, and the apparatus 200 may comprise a plurality of fluorescence nanofibers 204 (not shown) to receive each of the multiple fluorescence frequencies substantially simultaneously. Still further embodiments may be realized.

Figure 3:
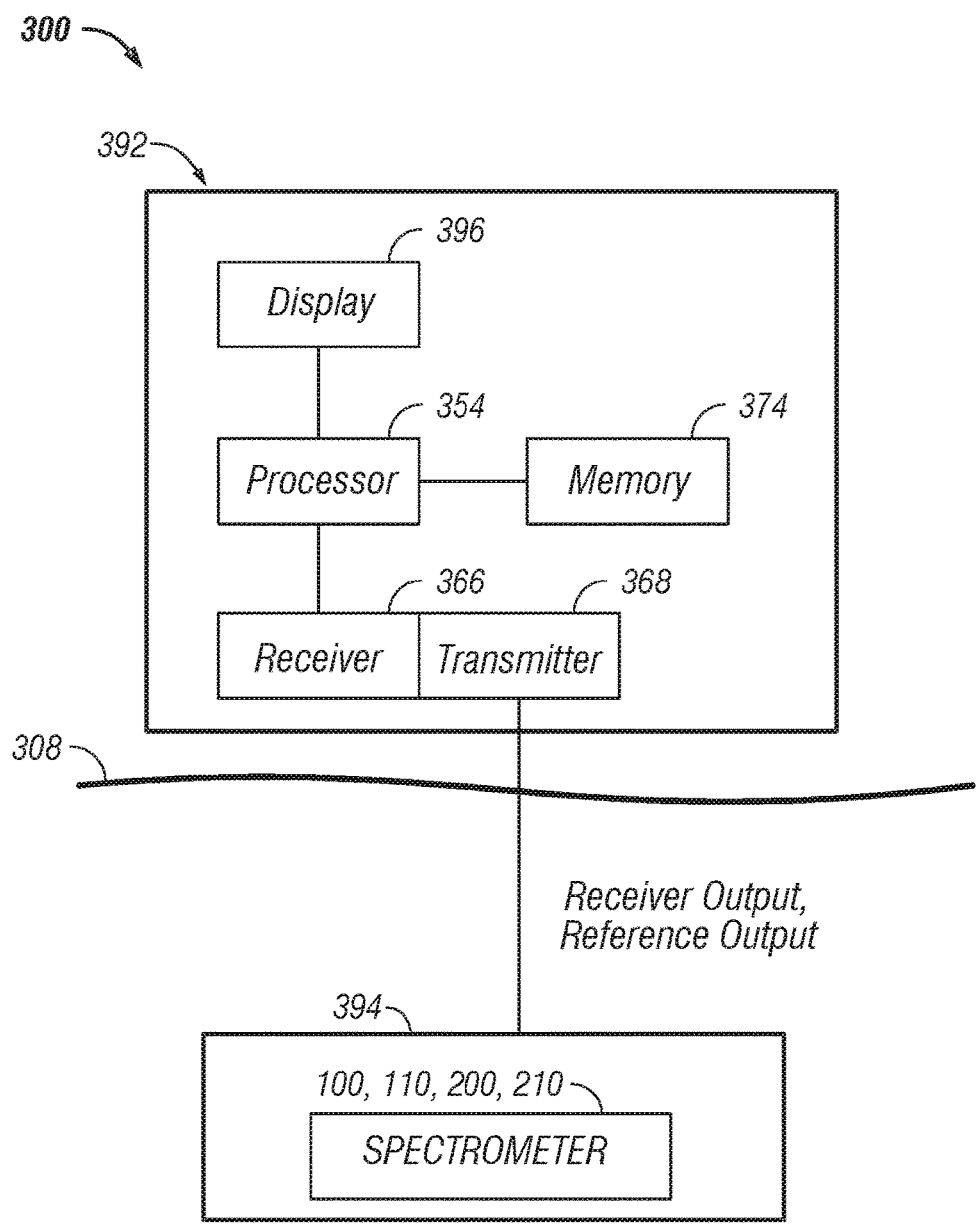
FIG. 3 illustrates a system block diagram according to various embodiments of the invention.

For example, FIG. 3 illustrates a system block diagram according to various embodiments of the invention. Here it can be seen that a system 300 may comprise a number of components, including a logging facility 392.

The logging facility 392, shown located above the surface 308, may comprise a processor 354 and a memory 374 coupled to the processor 354. The memory 374 may comprise instructions which, when executed, result in the system 300 accomplishing any of the methodologies described herein.

The system 300 may also comprise a housing 394, such as a down hole tool or tool body that is attached to and includes any one or more of the components shown in FIGS. 1-2. Thus, the system 300 can form part of a subsurface exploration system, with a down hole tool used to house various components of the apparatus 100, 110, 200, 210. The housing 394 may therefore be attached to one or more energy sources (e.g., SC, SC0 . . . SC3 of FIGS. 1-2), one or more receivers (e.g., 136, 236 of FIGS. 1-2), and one or more pressure-tight chambers (e.g., 128, 228 of FIGS. 1-2), for example. In addition, one or more components of the logging facility 392 may be located below the surface 308, and included within the housing 394.

The facility 392 may comprise a receiver 366 and/or transmitter 368 to receive and transmit commands and data to the housing 394, and components located therein. A display 396 may be used display a variety of information, include a spectroscopic property of the sampled material determined as the result of comparisons made by the processor 354 between the various types of energy processed in the apparatus 100, 110, 200, 210 included in the housing 394.

Figure 4:
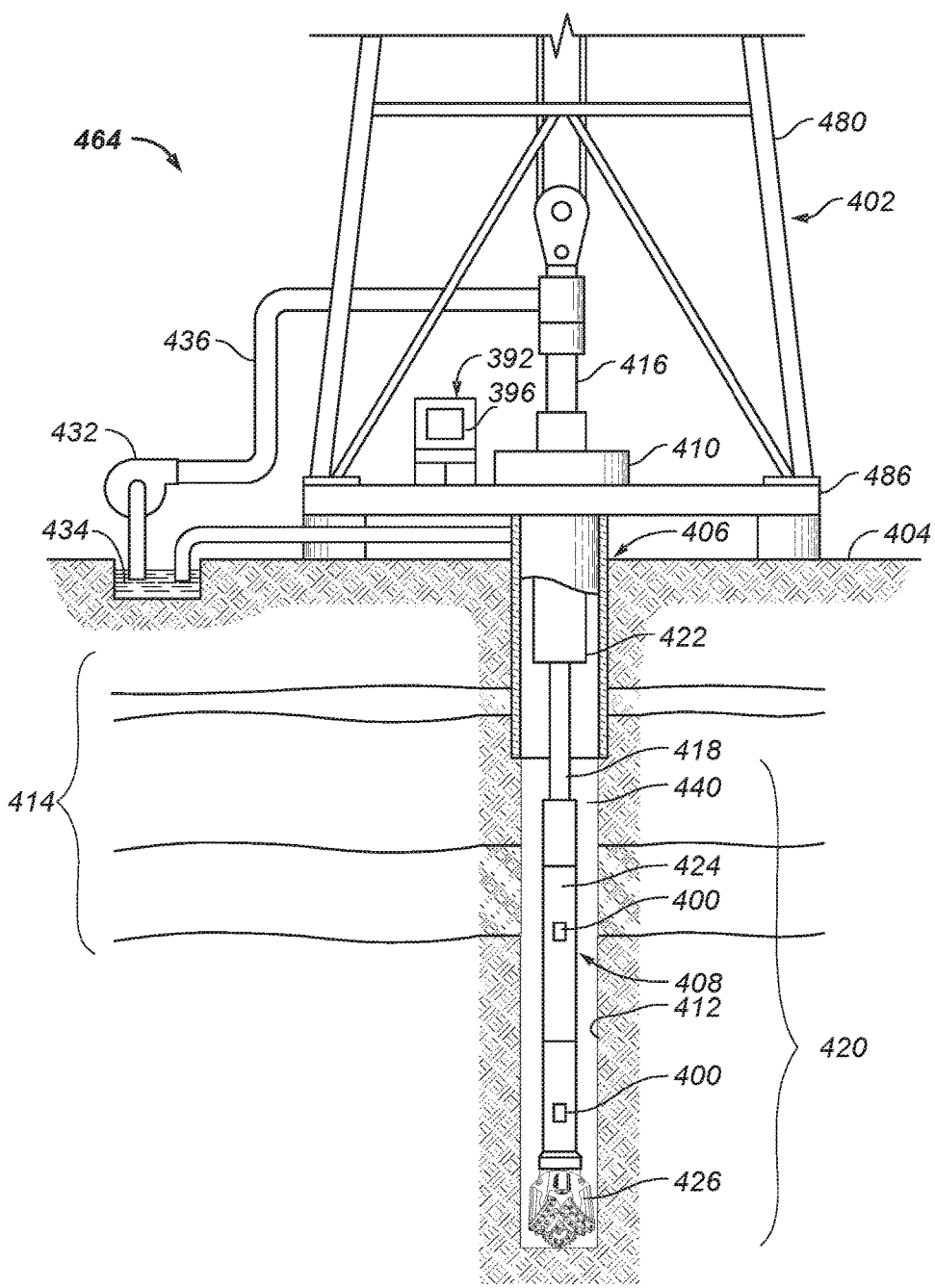
FIGS. 4-5 illustrate additional system embodiments of the invention.
Figure 5:
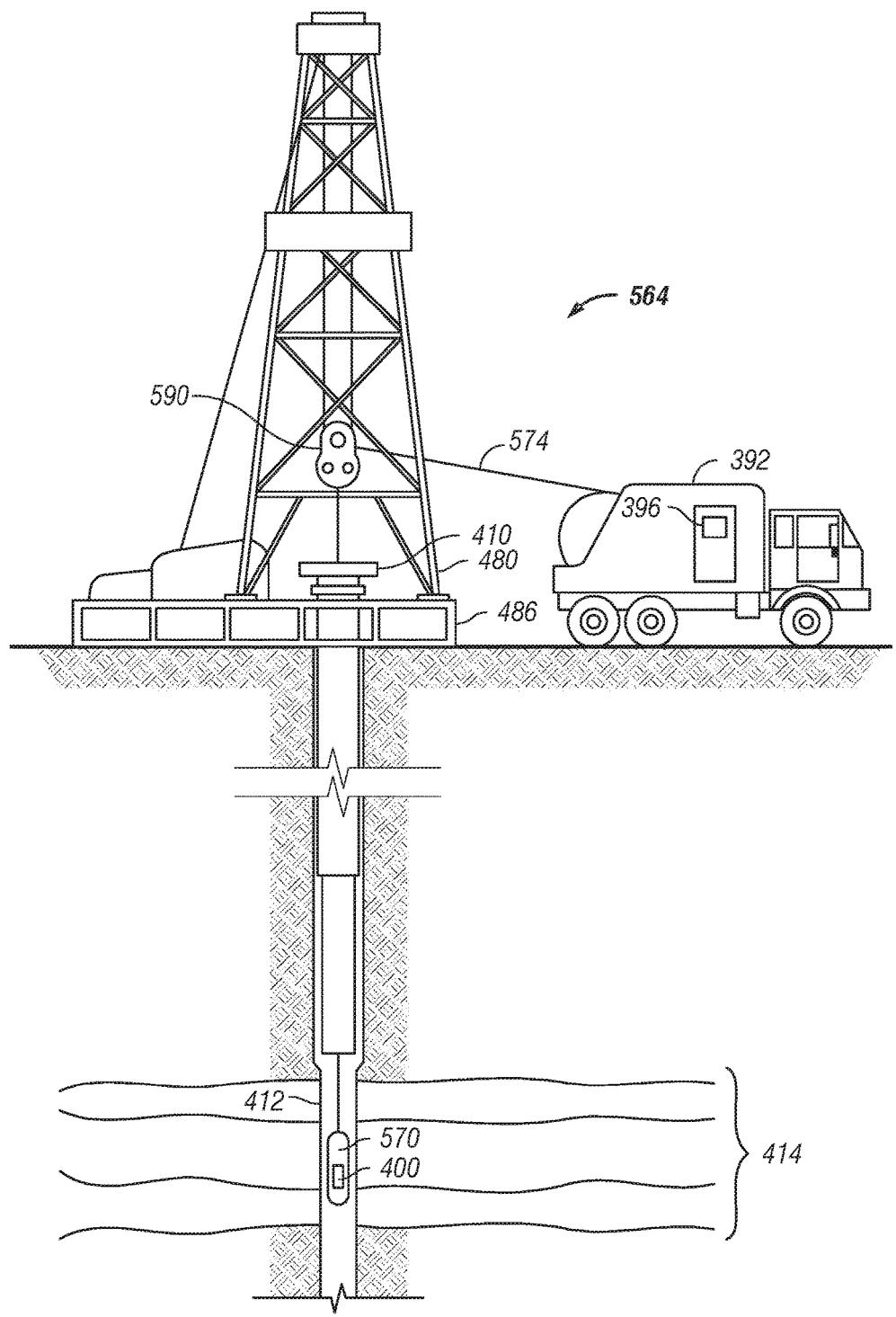

FIGS. 4-5 illustrate additional system embodiments of the invention. For example, FIG. 4 illustrates a system 464 as a drilling rig system embodiment of the invention, and FIG. 5 illustrates a system 564 as a wireline system embodiment of the invention. Thus, systems 464, 564 may comprise portions of a down hole tool 424 as part of a down hole drilling operation, or a tool body 570 as part of a wireline logging operation.

Drilling of oil and gas wells is commonly carried out using a string of drill pipes connected together so as to form a drilling string that is lowered through a rotary table 410 into a wellbore or borehole 412. Turning now to FIG. 4, it can be seen how a system 464 may form a portion of a drilling rig 402 located at the surface 404 of a well 406. The drilling rig 402 may provide support for a drill string 408. The drill string 408 may operate to penetrate a rotary table 410 for drilling a borehole 412 through subsurface formations 414. The drill string 408 may include a Kelly 416, drill pipe 418, and a bottom hole assembly 420, perhaps located at the lower portion of the drill pipe 418. In some embodiments, one or more instruments 400, similar to or identical to the system 300 of FIG. 3, may be carried and thus attached to the drill string 408 or the down hole tool 424.

The bottom hole assembly 420 may include drill collars 422, a down hole tool 424, and a drill bit 426. The drill bit 426 may operate to create a borehole 412 by penetrating the surface 404 and subsurface formations 414. The down hole tool 424 may comprise any of a number of different types of tools including MWD (measurement while drilling) tools, LWD (logging while drilling) tools, and others.

During drilling operations, the drill string 408 (perhaps including the Kelly 416, the drill pipe 418, and the bottom hole assembly 420) may be rotated by the rotary table 410. In addition to, or alternatively, the bottom hole assembly 420 may also be rotated by a motor (e.g., a mud motor) that is located down hole. The drill collars 422 may be used to add weight to the drill bit 426. The drill collars 422 may also operate to stiffen the bottom hole assembly 420, allowing the bottom hole assembly 420 to transfer the added weight to the drill bit 426, and in turn, to assist the drill bit 426 in penetrating the surface 404 and subsurface formations 414.

During drilling operations, a mud pump 432 may pump drilling fluid (sometimes known by those of skill in the art as "drilling mud") from a mud pit 434 through a hose 436 into the drill pipe 418 and down to the drill bit 426. The drilling fluid can flow out from the drill bit 426 and be returned to the surface 404 through an annular area 440 between the drill pipe 418 and the sides of the borehole 412. The drilling fluid may then be returned to the mud pit 434, where such fluid is filtered. In some embodiments, the drilling fluid can be used to cool the drill bit 426, as well as to provide lubrication for the drill bit 426 during drilling operations. Additionally, the drilling fluid may be used to remove subsurface formation 414 cuttings created by operating the drill bit 426.

FIG. 5 shows a well during wireline logging operations. A drilling platform 486 is equipped with a derrick 480 that supports a hoist 590. Here it is assumed that the drilling string has been temporarily removed from the borehole 412 to allow a wireline logging tool body 570, such as a probe or sonde that carries one or more instruments 400, to be lowered by wireline or logging cable 574 into the borehole 412. Typically, the tool body 570 is lowered to the bottom of the region of interest and subsequently pulled upward at a substantially constant speed.

During the upward trip, the instruments 400 included in the tool body 570 may be used to perform measurements in the borehole 412 as they pass by. The measurement data can be communicated to a surface logging facility 392 for storage, processing, and analysis.

The logging facility 392 may be provided with electronic equipment, such any one or more of the components of the system 300 in FIG. 3, including one or more components of the apparatus 100, 110, 200, 210 of FIGS. 1-2.

The systems 464, 564 of FIGS. 4 and 5 may comprise a display 396. The measurement data provided to the facility 392 and displayed on the display 396 may include data similar to that which is gathered and analyzed during drilling operations (e.g., during LWD operations). Such data may include derived data, including material or chemical properties of sampled material disposed proximate to the sampling nanofiber 104 or fluorescence nanofiber 204 used in the apparatus 100, 110, 200, 210 of FIGS. 1-2.

The apparatus 100, 110, 200, 210; nanofibers 104, 116, 204; ends 108, 112, 120, 124, 208, 212, 220, 224, 262, 264; surfaces 130, 132, 230, 232; chambers 128, 228; receivers 136, 236; sampled material 140, 240; barriers 144, 244; energy 154, 254; probe fiber 260; systems 300, 464, 564; surface 308; processor 354; receiver 366; transmitter 368; memory 374; logging facility 392; display 396; instrument 400; drilling rig 402; well 406; drill string 408; rotary table 410; borehole 412; formation 414; Kelly 416; drill pipe 418; bottom hole assembly 420; drill collars 422; down hole tool 424; drill bit 426; mud pump 432; mud pit 434; hose 436; systems 464, 564; tool body 570; drilling platform 486; derrick 480; logging cable 574; hoist 590; balancing bridge BB; input CAL; multiplexer MUX; outputs PNO, RRO, RVO; power normalizer PN; reference detector RD; regression module RR; and energy sources SC, SC0, SC1, . . . SC3 may all be characterized as "modules" herein. Such modules may include hardware circuitry, and/or a processor and/or memory circuits, software program modules and objects, and/or firmware, and combinations thereof, as desired by the architect of the apparatus 100, 110, 200, 210; instruments 400; and systems 300·464, 564, and as appropriate for particular implementations of various embodiments. For example, in some embodiments, such modules may be included in an apparatus and/or system operation simulation package, such as a software electrical signal simulation package, a power usage and distribution simulation package, a power/heat dissipation simulation package, and/or a combination of software and hardware used to simulate the operation of various potential embodiments.

It should also be understood that the apparatus and systems of various embodiments can be used in applications other than for logging operations, and thus, various embodiments are not to be so limited. The illustrations of apparatus 100, 110, 200, 210; instruments 400; and systems 300, 464, 564 are intended to provide a general understanding of the structure of various embodiments, and they are not intended to serve as a complete description of all the elements and features of apparatus and systems that might make use of the structures described herein.

Applications that may incorporate the novel apparatus and systems of various embodiments include a variety of electronic systems, such as televisions, cellular telephones, personal computers, workstations, radios, video players, vehicles, and location technology (e.g., GPS (Global Positioning System) location technology), signal processing for geothermal tools and smart transducer interface node telemetry systems, among others. Some embodiments include a number of methods.

Figure 6:
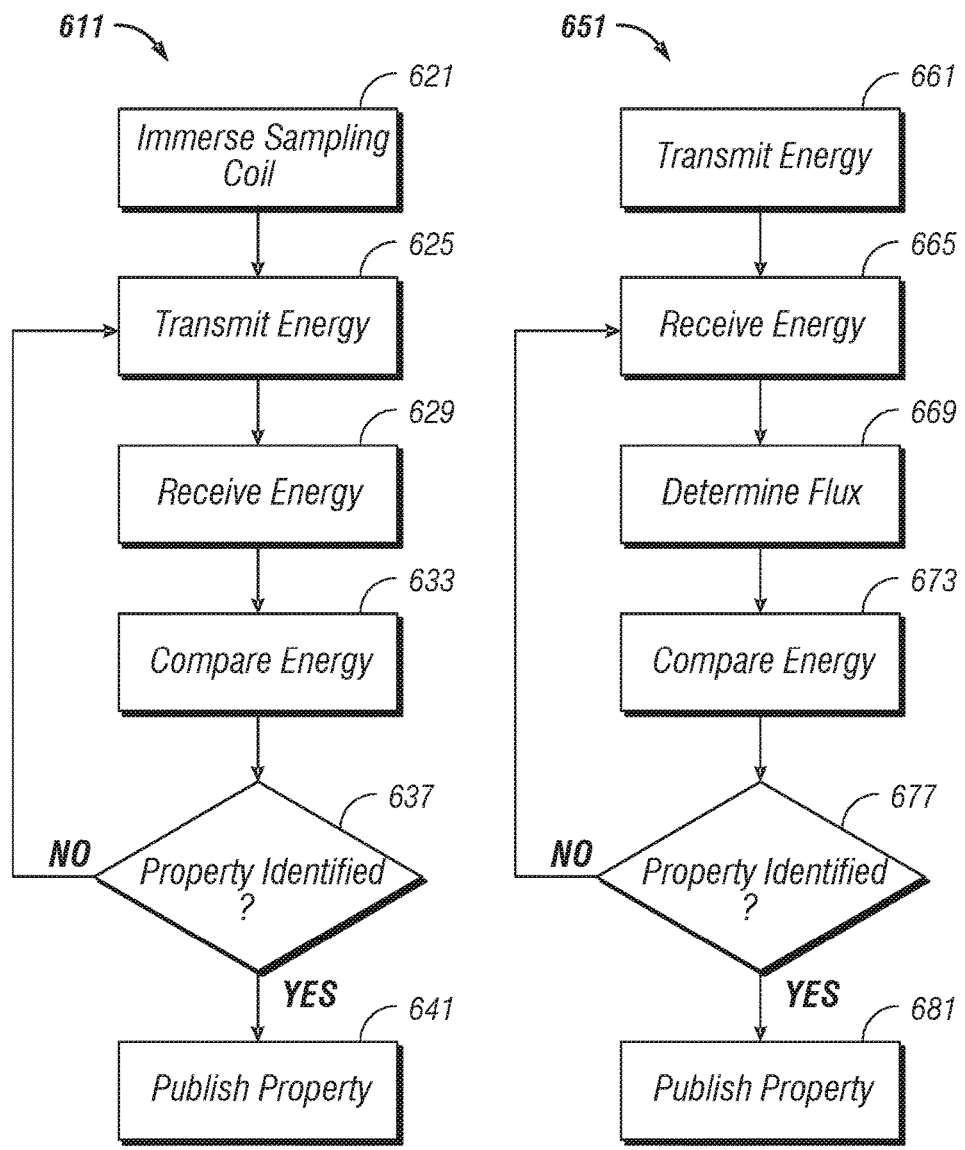
FIG. 6 includes flow charts illustrating several methods according to various embodiments of the invention.

FIG. 6 includes flow charts illustrating several methods 611, 651 according to various embodiments of the invention. For example, a processor-implemented method 611 to execute on one or more processors that perform a method to determine a spectroscopic property of a material based on direct interaction with evanescent radiation may begin at block 621. The activity at block 621 may include immersing a sampling coil in a downhole fluid located outside a pressure-tight chamber that houses an energy source. The method 611 may continue on to block 625 with transmitting energy, using the energy source, to a first sampling end of a nanofiber sampling coil and/or a first reference end of a nanofiber reference coil.

At block 629, the method 611 may include receiving the energy modified by evanescent interaction with a sampled material located within an inner diameter or outside of an outer diameter of the sampling coil, and/or receiving the energy modified by propagation through the reference coil.

The activity at block 629 may further comprise multiplexing reception through a plurality of sampling coils, including the sampling coil, wherein at least two of the plurality of sampling coils have different coil diameters.

At block 633, the method 611 may include comparing the energy modified by evanescent interaction with the energy modified by propagation through the reference coil to determine a spectroscopic property of the sampled material.

Thus, the sampled material can be located inside or outside of the sampling coil. In either case, the properties of the material can be determined based on the received intensity of the resultant energy, as compared with the energy from the reference.

The method 611 may go on to block 637 to include determining whether a specific spectroscopic property of the sampled material has been identified. If not, then the method may go on to block 625 with continued transmission of the energy, provoking further interaction between the evanescent radiation and the sampled material.

If a desired spectroscopic property is identified at block 637, then the method 611 may continue on to block 641 with publishing a material property or a chemical property of the sampled material based on the spectroscopic property. Publication may occur to a display, as noted above, to a memory, or to a printer.

While the terms "sampling coil", "reference coil" have been used with respect to the method 611, it should be noted that this has been done as a matter of convenience, and not limitation. Sampling nanofibers and reference nanofibers may or may not be formed into coils in various embodiments, as desired.

Additional embodiments may be realized. For example, a processor-implemented method 651 to execute on one or more processors that perform a method to determine a spectroscopic property of a material based on indirect interaction with evanescent radiation (e.g., fluorescence induced by evanescent radiation) may begin at block 661. The activity at block 661 may include transmitting source energy having a selected fluorescence frequency to a first fluorescence end of a fluorescence nanofiber to induce evanescent energy along at least a portion of the fluorescence nanofiber.

The method 651 may continue on to block 665 to include receiving fluorescence energy received by a probe fiber disposed proximate to a sampled material, wherein the sampled material is disposed proximate to the fluorescence nanofiber.

The sampled material provides fluorescence energy in response to the evanescent energy it receives. As is the case with method 611, the sampled material might comprise formation fluid or drilling fluid. In some embodiments, one end of the probe fiber receives the fluorescence energy. In some embodiments, an unclad portion of the probe fiber receives the fluorescence energy.

At block 669, the method 651 may include determining flux in a flow of the sampled material using multiple fluorescence nanofibers disposed along a substantially straight line.

The method 651 may go on to include, at block 673, comparing the fluorescence energy with the source energy received at a reference fiber to determine a spectroscopic property of the sampled material. It should be noted that while the use of a reference fiber is included in this particular embodiment, not all embodiments make use of a reference fiber. The fluorescence energy can be compared to one or more values stored in memory, for example, to determine a spectroscopic property of the sampled material.

The method 651 may go on to block 677 to include determining whether a specific spectroscopic property has been identified. If not, then the method may go on to block 665 to include continued reception of the fluorescence energy emitted by the sampled material.

If a desired spectroscopic property is identified at block 677, then the method 651 may continue on to block 681 with publishing a material property or a chemical property of the sampled material based on the spectroscopic property. Publication may occur to a display, as noted above, to a memory, or to a printer. That is, properties of the sampled material can be determined based on the received intensity of the fluorescence energy, as compared with the intensity of the energy provided by the fiber, or some value stored in memory.

It should be noted that the methods described herein do not have to be executed in the order described, or in any particular order. Moreover, various activities described with respect to the methods identified herein can be executed in iterative, serial, or parallel fashion. Some activities described for one method may be added to another, and some of the included activities may be left out. Information, including parameters, commands, operands, and other data, can be sent and received in the form of one or more carrier waves.

Figure 7:
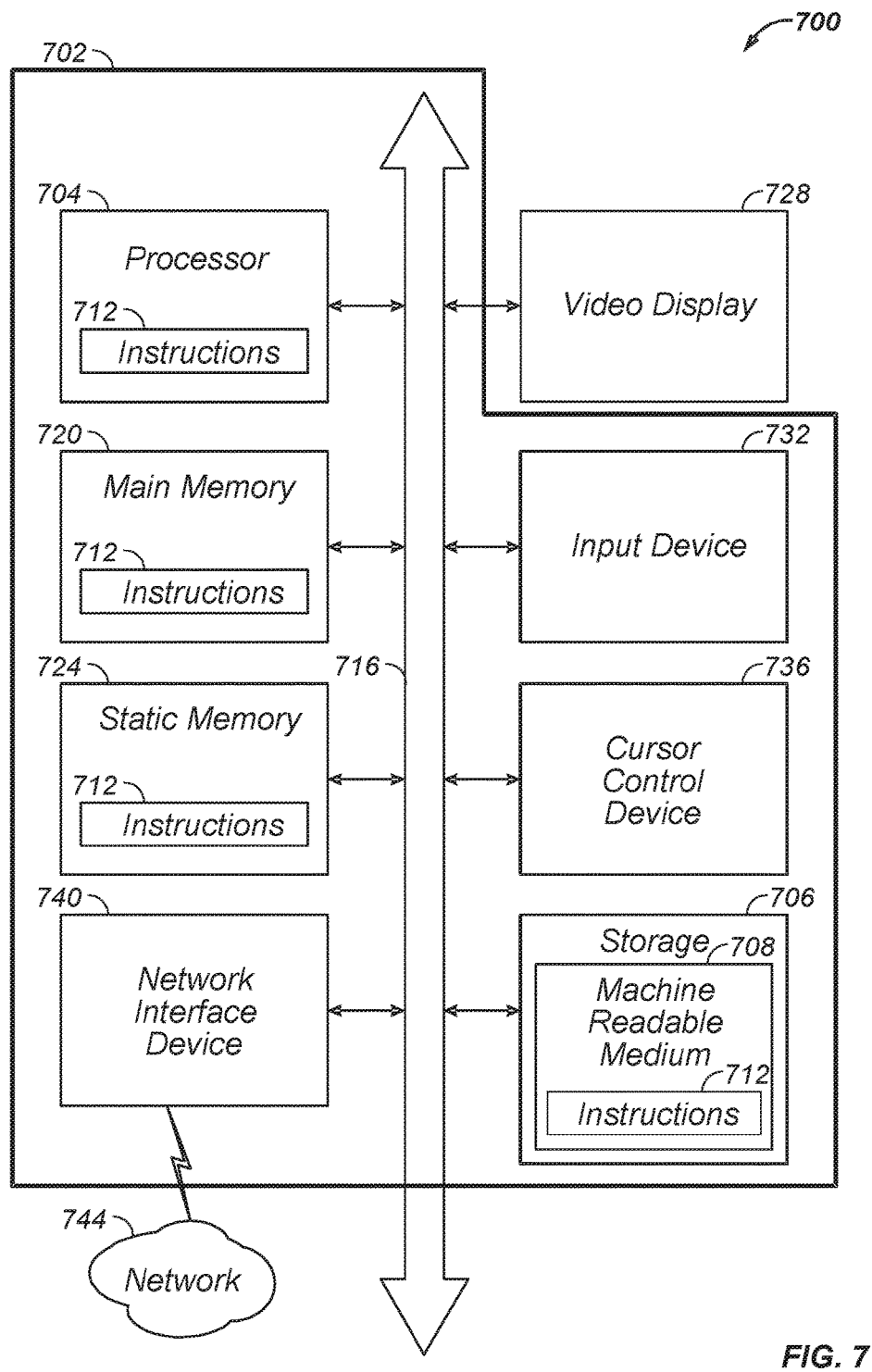
FIG. 7 is a block diagram of an article according to various embodiments of the invention.

FIG. 7 is a block diagram of an article 700 of manufacture, including a specific machine 702, according to various embodiments of the invention. Upon reading and comprehending the content of this disclosure, one of ordinary skill in the art will understand the manner in which a software program can be launched from a computer-readable medium in a computer-based system to execute the functions defined in the software program.

One of ordinary skill in the art will further understand the various programming languages that may be employed to create one or more software programs designed to implement and perform the methods disclosed herein. The programs may be structured in an object-orientated format using an object-oriented language such as Java or C++. Alternatively, the programs can be structured in a procedure-orientated format using a procedural language, such as assembly or C. The software components may communicate using any of a number of mechanisms well known to those of ordinary skill in the art, such as application program interfaces or interprocess communication techniques, including remote procedure calls. The teachings of various embodiments are not limited to any particular programming language or environment. Thus, other embodiments may be realized.

For example, an article 700 of manufacture, such as a computer, a memory system, a magnetic or optical disk, some other storage device, and/or any type of electronic device or system may include one or more processors 704 coupled to a machine-readable medium 708 such as a memory (e.g., removable storage media, as well as any memory including an electrical, optical, or electromagnetic conductor comprising tangible media) having instructions 712 stored thereon (e.g., computer program instructions), which when executed by the one or more processors 704 result in the machine 702 performing any of the actions described with respect to the processes or methods described above.

The machine 702 may take the form of a specific computer system having a processor 704 coupled to a number of components directly, and/or using a bus 716. Thus, the machine 702 may be similar to or identical to the system 300 in FIG. 3, or the logging facility 392 shown in FIGS. 3-5.

Turning now to FIG. 7, it can be seen that the components of the machine 702 may include main memory 720, static or non-volatile memory 724, and mass storage 706. Other components coupled to the processor 704 may include an input device 732, such as a keyboard, or a cursor control device 736, such as a mouse. An output device 728, such as a video display, may be located apart from the machine 702 (as shown), or made as an integral part of the machine 702.

A network interface device 740 to couple the processor 704 and other components to a network 744 may also be coupled to the bus 716. The instructions 712 may be transmitted or received over the network 744 via the network interface device 740 utilizing any one of a number of well-known transfer protocols (e.g., HyperText Transfer Protocol). Any of these elements coupled to the bus 716 may be absent, present singly, or present in plural numbers, depending on the specific embodiment to be realized.

The processor 704, the memories 720, 724, and the storage device 706 may each include instructions 712 which, when executed, cause the machine 702 to perform any one or more of the methodologies described herein. In some embodiments, the machine 702 operates as a standalone device or may be connected (e.g., networked) to other machines. In a networked environment, the machine 702 may operate in the capacity of a server or a client machine in server-client network environment, or as a peer machine in a peer-to-peer (or distributed) network environment.

The machine 702 may comprise a personal computer (PC), a workstation, a tablet PC, a set-top box (STB), a PDA, a cellular telephone, a web appliance, a network router, switch or bridge, server, client, or any specific machine capable of executing a set of instructions (sequential or otherwise) that direct actions to be taken by that machine to implement the methods and functions described herein. Further, while only a single machine 702 is illustrated, the term "machine" shall also be taken to include any collection of machines that individually or jointly execute a set (or multiple sets) of instructions to perform any one or more of the methodologies discussed herein.

While the machine-readable medium 708 is shown as a single medium, the term "machine-readable medium" should be taken to include a single medium or multiple media (e.g., a centralized or distributed database, and/or associated caches and servers, and or a variety of storage media, such as the registers of the processor 704, memories 720, 724, and the storage device 706 that store the one or more sets of instructions 712. The term "machine-readable medium" shall also be taken to include any medium that is capable of storing, encoding or carrying a set of instructions for execution by the machine and that cause the machine 702 to perform any one or more of the methodologies of the present invention, or that is capable of storing, encoding or carrying data structures utilized by or associated with such a set of instructions. The terms "machine-readable medium" or "computer-readable medium" shall accordingly be taken to include tangible media, such as solid-state memories and optical and magnetic media.

Various embodiments may be implemented as a stand-alone application (e.g., without any network capabilities), a client-server application or a peer-to-peer (or distributed) application. Embodiments may also, for example, be deployed by Software-as-a-Service (SaaS), an Application Service Provider (ASP), or utility computing providers, in addition to being sold or licensed via traditional channels.

Using the apparatus, systems, and methods disclosed, those in the petroleum recovery industry and other industries may now be able to determine spectroscopic properties of various sampled materials more readily. The analyses conducted may thus benefit from results that are obtained with increased accuracy and efficiency.

The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The Abstract of the Disclosure is provided to comply with 37 C.F.R. § 1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate embodiment.

What is claimed is:

1. An apparatus, comprising:
    a plurality of sampling optical nanofibers, each of the sampling optical nanofibers formed into a sampling optical nanofiber coil having a first sampling end and a second sampling end;
    at least one reference nanofiber formed into a reference optical nanofiber coil having a first reference end and a second reference end;
    a pressure-tight chamber defined by an inner surface that is completely enclosed by an outer surface, the first and the second sampling ends disposed within the pressure-tight chamber, each of the sampling optical nanofiber coils disposed outside the pressure-tight chamber in a region open to fluid flow to sample the fluid;
    an optical energy source to direct optical energy to the first sampling ends and the first reference end, the optical energy source disposed in the pressure-tight chamber; and
    a receiver arranged to receive, from each of the second sampling ends, optical energy resulting from the optical energy transmitted to each of the first sampling ends being modified by evanescent interaction with sample material located within an inner diameter of the sampling optical nanofiber coils or outside an outer diameter of the sampling optical nanofiber coils, and to receive, from the second reference end, optical energy resulting from the optical energy transmitted to the first reference end being modified by propagation through the reference coil.

2. The apparatus of claim 1, wherein the optical energy source comprises:
    a plurality of broadband optical sources having substantially orthogonal wave functions.

3. The apparatus of claim 2, wherein the plurality of broadband optical sources is arranged to direct the optical energy from each one of the broadband optical sources to one of a corresponding plurality of reference optical nanofibers that includes the at least one reference optical nanofiber.

4. The apparatus of claim 1, wherein the optical energy source comprises a broadband optical energy source, and wherein the receiver comprises:
    one of a tunable receiver to resolve a plurality of wavelengths in the optical energy provided by the broadband optical energy source or a plurality of receivers corresponding to a plurality of reception wavelength sensitivities.

5. The apparatus of claim 1, wherein the optical energy source comprises:
    one of a single broadband optical source or a plurality of substantially monochromatic optical sources to provide the optical energy.

6. The apparatus of claim 1, wherein the optical energy source comprises:
    one of a broadband optical source or a substantially monochromatic optical source.

7. The apparatus of claim 1, wherein the optical energy source comprises:
    a frequency tunable, substantially monochromatic optical source.

8. The apparatus of claim 1, wherein the reference optical nanofiber coil is disposed outside the chamber.

9. The apparatus of claim 1, wherein at least two of the plurality of sampling optical nanofiber coils have different coil diameters corresponding to different sensitivity wavelengths, and a spacing between loops in the at least two of the plurality of sampling optical nanofiber coils is greater than one evanescent wavelength associated with one of the at least two of the plurality of sampling optical nanofiber coils.

10. The apparatus of claim 1, wherein the sampling optical nanofiber coils are at least partially coated with a pH-selective compound or an ion-selective compound.

11. A system comprising:
a downhole tool; and
an apparatus attached to the downhole tool, the apparatus including a plurality of sampling optical nanofibers, each of the sampling optical nanofibers formed into a sampling optical nanofiber coil having a first sampling end and a second sampling end;
at least one reference optical nanofiber formed into a reference optical nanofiber coil having a first reference end and a second reference end;
a pressure-tight chamber defined by an inner surface that is completely enclosed by an outer surface, the first and the second sampling ends disposed within the pressure-tight chamber, each of the optical nanofiber sampling coils disposed outside the pressure-tight chamber in a region open to downhole fluid flow to sample the downhole fluid;
an optical energy source arranged to direct optical energy to the first sampling ends and the first reference end, the optical energy source disposed in the pressure-tight chamber; and
a receiver arranged to receive, from each of the second sampling ends, optical energy resulting from the optical energy transmitted to each of the first sampling ends being modified by evanescent interaction with sample material located within an inner diameter of the sampling optical nanofiber coils or outside an outer diameter of the sampling optical nanofiber coils, and to receive, from the second reference end, optical energy resulting from the optical energy transmitted to the first reference end being modified by propagation through the reference optical nanofiber coil.

12. The system of claim 11, further comprising:
a balancing bridge coupled to one of the sampling optical nanofibers and the at least one reference optical nanofiber.

13. The system of claim 11, further comprising:
the receiver having a plurality of detectors with specific wavelength response factors, the detectors configured to create a multivariate signal as the receiver output; and
one or more processors configured to compare the electromagnetic energy modified by evanescent interaction with the sampled downhole fluid with the electromagnetic energy modified by propagation through the reference optical nanofiber coil and to provide a regression output based on a calibration input and the receiver output, to determine a spectroscopic property of the sampled downhole fluid.

14. The system of claim 11, further comprising:
a wavelength discriminator interposed between the second sampling ends and the receiver.

15. The system of claim 11, wherein the optical energy source comprises:
a plurality of optical energy sources coupled to a multiple-input, single-output multiplexer.

16. The system of claim 11, further comprising:
a ferromagnetic seal to seal the plurality of sampling optical nanofibers against the inner surface.

17. A method comprising:
immersing a plurality of sampling optical nanofibers in a downhole fluid located outside a pressure-tight chamber in a region in a borehole open to fluid flow, the pressure-tight chamber housing an energy source used to provide optical energy, each of the sampling optical nanofibers formed into a sampling optical nanofiber coil, the sampling optical nanofiber coil being immersed in the downhole fluid to sample the downhole fluid;
transmitting the optical energy to a first sampling end of each sampling optical nanofiber of the plurality of sampling optical nanofibers, each of the sampling optical nanofibers having a second sampling end, the first sampling ends and the second sampling ends disposed in the pressure-tight chamber housing the energy source;
transmitting energy to a first reference end of a reference optical nanofiber formed into a reference optical nanofiber coil having a second reference end;
receiving, from each second sampling end, optical energy resulting from the optical energy transmitted to each first sampling end being modified by evanescent interaction with sample material located within an inner diameter or outside of an outer diameter of the sampling optical nanofiber coils;
receiving, from the second reference end, optical energy resulting from the optical energy transmitted to the first reference end being modified by propagation through the reference optical nanofiber coil; and
comparing the optical energy modified by evanescent interaction of each sampling optical nanofiber coil with the optical energy modified by propagation through the reference optical nanofiber coil to determine a spectroscopic property of the sampled material.

18. The method of claim 17, further comprising:
publishing a material property or a chemical property of the sampled material based on the spectroscopic property.

19. The method of claim 17, wherein transmitting optical energy comprises:
transmitting the optical energy to the sampling optical nanofiber coils wherein at least two of the plurality of sampling optical nanofiber coils have different coil diameters.

\* \* \* \* \*